(12) United States Patent
Gand

(10) Patent No.: US 11,484,243 B2
(45) Date of Patent: Nov. 1, 2022

(54) PORTABLE ALZHEIMER DETECTOR

(71) Applicant: Francois Gand, Guelph (CA)

(72) Inventor: Francois Gand, Guelph (CA)

(73) Assignee: NURO CORP., Guelph (CA)

( * ) Notice: Subject to any disclaimer, the term of this patent is extended or adjusted under 35 U.S.C. 154(b) by 810 days.

(21) Appl. No.: 16/324,608

(22) PCT Filed: Aug. 11, 2017

(86) PCT No.: PCT/CA2017/000189
§ 371 (c)(1),
(2) Date: Feb. 11, 2019

(87) PCT Pub. No.: WO2018/027298
PCT Pub. Date: Feb. 15, 2018

(65) Prior Publication Data
US 2019/0183403 A1    Jun. 20, 2019

Related U.S. Application Data

(60) Provisional application No. 62/374,287, filed on Aug. 12, 2016.

(51) Int. Cl.
*A61B 5/00* (2006.01)
*A61B 8/08* (2006.01)
(Continued)

(52) U.S. Cl.
CPC .......... *A61B 5/4088* (2013.01); *A61B 5/0002* (2013.01); *A61B 5/0075* (2013.01); *A61B 5/0261* (2013.01); *A61B 5/14553* (2013.01); *A61B 5/4064* (2013.01); *A61B 5/6814* (2013.01); *A61B 5/7267* (2013.01); *A61B 5/7275* (2013.01); *A61B 8/0808* (2013.01); *A61B 8/0816* (2013.01); *A61B 8/0891* (2013.01); *A61B 8/4227* (2013.01); *A61B 8/488* (2013.01); *A61B 8/5223* (2013.01);
(Continued)

(58) Field of Classification Search
None
See application file for complete search history.

(56) References Cited

U.S. PATENT DOCUMENTS

| 5,724,987 A | 3/1998 | Gevins et al. |
| 6,947,790 B2 | 9/2005 | Gevins et al. |

(Continued)

FOREIGN PATENT DOCUMENTS

| CA | 2873688 A1 | 7/2013 |
| CA | 2960148 A1 | 3/2016 |

OTHER PUBLICATIONS

WIPO, International Search Report and Written Opinion for PCT Application No. PCT/CA2017/000189 dated Nov. 2, 2017.

*Primary Examiner* — Yi-Shan Yang
(74) *Attorney, Agent, or Firm* — Norton Rose Fulbright Canada LLP

(57) ABSTRACT

A device is provided for diagnostic measurement by simultaneous multimodal analysis of a subject's head wherein the cerebral blood flow variations as well as the concentration level of oxygenation in the subject's blood are used to determine the presence and the pathophysiology of neurocognitive disorders, including the neurodegenerative disease referred to as Alzheimer's disease.

24 Claims, 10 Drawing Sheets

(51) Int. Cl.
*A61B 5/026* (2006.01)
*A61B 5/1455* (2006.01)
*A61B 8/00* (2006.01)
*G16H 50/30* (2018.01)
*G16H 50/20* (2018.01)
*G16H 40/67* (2018.01)
*G16H 10/60* (2018.01)
*G16H 15/00* (2018.01)
*G16H 20/40* (2018.01)

(52) U.S. Cl.
CPC ............. *A61B 8/565* (2013.01); *G16H 10/60* (2018.01); *G16H 15/00* (2018.01); *G16H 20/40* (2018.01); *G16H 40/67* (2018.01); *G16H 50/20* (2018.01); *G16H 50/30* (2018.01)

(56) References Cited

U.S. PATENT DOCUMENTS

| | | |
|---|---|---|
| 9,269,046 B2 | 2/2016 | Rothman |
| 9,357,941 B2 | 6/2016 | Simon |
| 2009/0177092 A1* | 7/2009 | Riechers ............. A61B 5/0035 600/459 |
| 2012/0289869 A1* | 11/2012 | Tyler ..................... A61B 5/369 601/2 |
| 2013/0338544 A1* | 12/2013 | Newell .................... A61N 7/02 601/2 |
| 2015/0223731 A1* | 8/2015 | Sahin ................... A61B 5/1123 600/301 |
| 2015/0313496 A1 | 11/2015 | Connor |
| 2016/0239084 A1 | 8/2016 | Connor |
| 2018/0239430 A1* | 8/2018 | Tadi ....................... H01L 33/58 |

* cited by examiner

PORTABLE ALZHEIMER DETECTOR

CROSS REFERENCE

This application claims the benefit of National Stage Entry from PCT Patent Application no. PCT/CA2017/000189, of the same title, filed Aug. 11, 2017, which claims priority from U.S. provisional application 62/374,287, filed Aug. 12, 2016, which application is incorporated herein in its entirety by this reference.

FIELD

The present application relates to medical devices, in particular to devices for detecting illnesses.

BACKGROUND

Alzheimer's disease is currently an irreversible, unpreventable and incurable disease, estimated in 2010 as the third leading cause of death behind heart disease and cancer in the United States and confirmed as the third leading cause of death in high-income economies worldwide in 2015 behind heart disease and stroke, with only one in four people with the disease being diagnosed. It is one of the most expensive conditions to society with a cost of caring for dementia-affected patients projected to cross $1 trillion by 2018 in the United States alone.

Furthermore, it has been established that the anatomical structure of the brain and its functioning degenerate permanently as the disease advances. As such the hope of protecting one's brain lessens the longer detection of a neurocognitive disorder is delayed. Previously, an increase in beta-amyloid protein, a polypeptide containing 37 to 49 amino acid residues and whose amyloid fibrillary form is the primary component of amyloid plaques, was considered to be the first detectable sign of Alzheimer's disease. However, new therapeutic interventions can provide additional benefits prior to the point at which an increase in beta-amyloid protein may be detectable.

With the emergence of promising new therapeutic interventions for Alzheimer's disease, there is a need for a novel techniques and devices which facilitate more frequent and economical screening, monitoring and earlier diagnosing of Alzheimer's disease and by exclusion and classification other types of neurocognitive disorders.

SUMMARY

According to one aspect, there is provided a portable wireless medical-grade hardware device that permits the early detection of Alzheimer's disease or other forms of neurocognitive disorders including but not limited to vascular dementia, subcortical vascular dementia or frontotemporal dementia. This early detection may be performed via multimodal non-invasive measurement, monitoring, storing, analysis and reporting of key features such as cerebral blood flow and/or cerebral oxygen concentration levels via multimodal sensor modules. This may allow for simultaneous functional transcranial Doppler and functional near infrared spectroscopy analysis on one or more of: the frontal; temporal; parietal; occipital; and/or cerebellar sections of the human brain, which may then be used to validate via mathematical data analysis processes, a pathological diagnosis and a clinical stage of advancement of the Alzheimer's disease or another neurocognitive disorder on any human subject.

The frontal regions of the brain are involved in motor function, problem solving, spontaneity, memory, language, initiation, judgement, impulse control, and social and sexual behavior. Frontal lobe damage has been observed to impact on divergent thinking and problem solving ability. The temporal lobe, located behind the ear, is involved in processing the comprehension of sounds and spoken words, as well as emotion. Since it includes the hippocampus, it also is associated with different types of memory. When affected by neurocognitive disorders, the temporal lobe has been shown to cause changes in: hearing; memory; speech comprehension; and ability to sequence and organise. Located above the ear, the parietal region of the brain receives and interprets sensations of pain, pressure, temperature, touch, size and shape, and body part awareness. The parietal region has been observed to cause changes in: ability to perceive sensory input such as pressure and touch; spatial perception; and ability to process information, when affected by neurocognitive disorder. The occipital region is located in the back of the head and is responsible for organizing and arranging visual input. When affected by neurocognitive disorder, this region has been observed to cause difficulty recognizing common items such as clothing. Also located at the back of the head, the cerebellar brain region is linked to coordination, posture, speech, and motor functions. Neurocognitive disorder affecting this region can cause loss of coordination.

Clearly, an economical, accurate, rapid, and portable apparatus and method for detecting indicators of neurocognitive disorder in the brain while a patient is conducting activities controlled by one or more of the above-mentioned brain regions (as described herein) is desirable.

According to another aspect, there is provided a method of determining a probability that a human subject has Alzheimer's disease or another neurocognitive disorder, the method comprising: a) placing a headset comprising a plurality of sensors on the human subject's head; b) acquiring, by the sensors, a Cerebral Dataset for the human subject; c) transmitting the Cerebral Dataset according to a pre-determined data-transmission standard to a computational unit; and d) determining, by the computational unit and a supportive machine-learning data processing architecture, the probability that the human subject has Alzheimer's disease or another neurocognitive disorder based on the Cerebral Dataset and one or more historical datasets.

It should be appreciated that the term "Cerebral Dataset" is used throughout this specification as being inclusive of all data acquired in the assessed regions of the human brain as described herein, including but not limited to cerebral-based data and cerebellar-based data. Furthermore, it is to be understood that, prior to the assessment by the suggested architecture, any other available neurocognitive data, any cognitive test result, any other demographic and key biomarkers relevant to the patient in regards to Alzheimer's or any other neurocognitive disorder and a tracked progression of the illness over time should also be considered as additional inputs to be submitted to the architecture in a compatible format prior to the assessment taking place, such external information being in this case an addition to the Cerebral Dataset 18 to permit an even higher accuracy in the subsequent data processing and following algorithmic predictive analysis.

According to another aspect, there is provided a headset for collecting a Cerebral Dataset from a patient, the headset comprising: a plurality of arms for surrounding a head of the patient, wherein the plurality of arms comprises a plurality of multimodal sensors for obtaining the Cerebral Dataset; and a transceiver for transmitting the obtained Cerebral Dataset.

According to another aspect, there is provided a system for determining a probability that a patient has Alzheimer's disease or another neurocognitive disorder, the system comprising: a headset configured for mounting to the patient's head, the headset comprising: a plurality of sensors for obtaining a Cerebral Dataset from the patient; and a transceiver for transmitting the obtained Cerebral Dataset; a computational unit for receiving the Cerebral Dataset from the transceiver, the computational unit comprising a processor configured to launch a procedural data management instruction set to determine the probability that the patient has Alzheimer's disease or another neurocognitive disorder based on the Cerebral Dataset and one or more historical datasets.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

BRIEF DESCRIPTION

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures:

FIG. 1 is a schematic drawing of an example Portable Alzheimer's Disease Detection Device according to some embodiments.

FIG. 2 is a schematic lateral projection of an example Wireless Multimodal Sensor-based Headset 2 placed on top of a subject's head with a visual reference to the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9 according to some embodiments.

DETAILED DESCRIPTION

Figure 1:
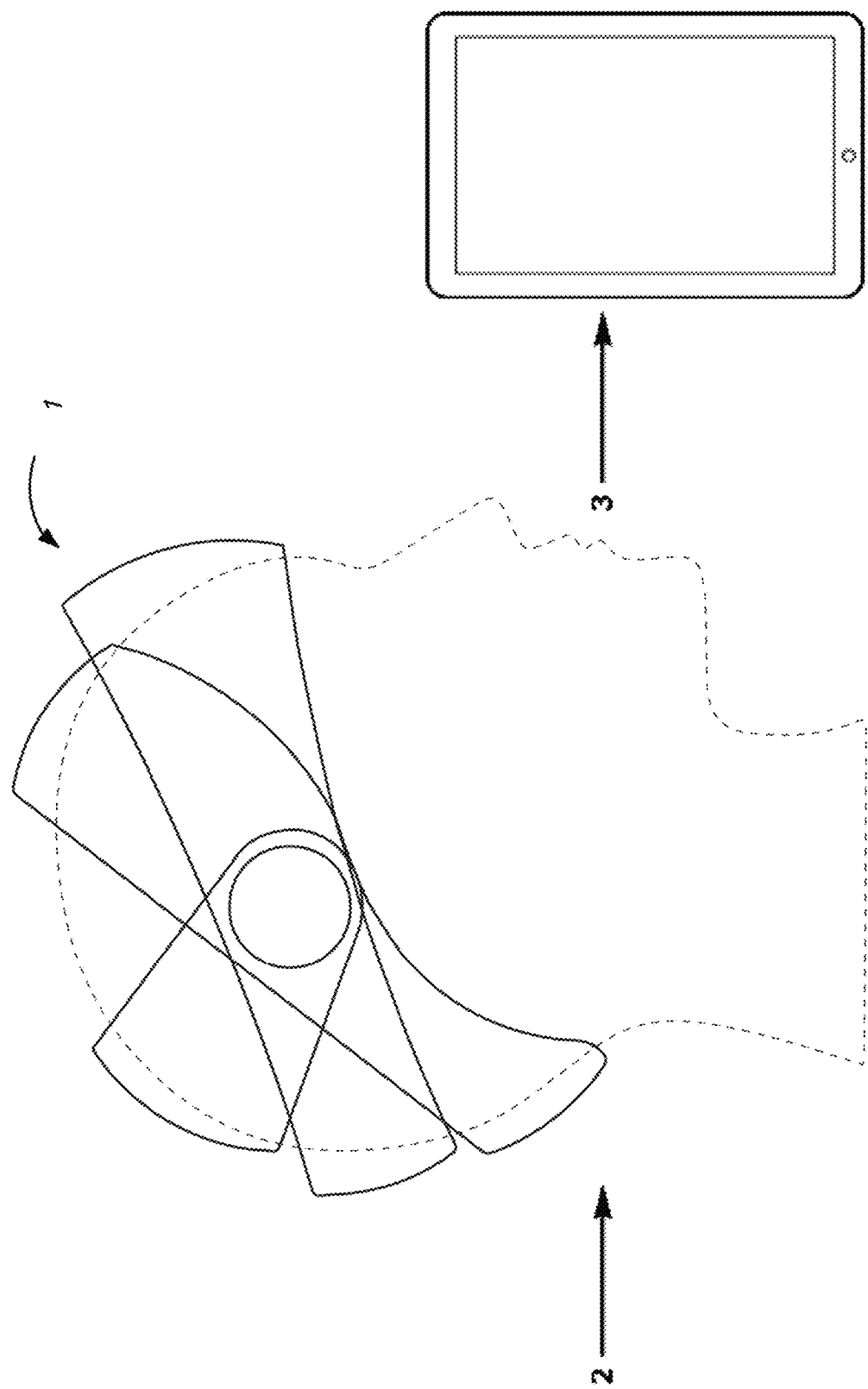

Embodiments of methods, systems, and apparatus are described through reference to the drawings.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Innovative, affordable, and/or portable means of providing early detection Alzheimer's are desirable. Such devices may, for example, aid in the provisioning of care of various individuals by detecting various values associated with Alzheimer's earlier than such detection may be available through existing means, and may also allow detection to be conducted on patients who, due to various reasons such as geographical location or lack of access to medical technologies, may not have access to other known detection means.

While the classical pathological hallmarks of Alzheimer's disease are amyloid beta plaques and tau proteins, recent academic research has found that, contrary to the previously-established understanding, an earlier physiological sign of Alzheimer's disease is a decrease in cerebral blood flow. Studies have shown that cerebrovascular changes are linked both to Alzheimer's disease pathogenesis and cognitive decline. Mild Cognitive Impairment (MCI) occurs with hypoperfusion, or reduced cerebral blood flow, to the relevant functional areas and can progress to Alzheimer's disease.

Cerebrovascular changes found in people with Mild Cognitive Impairment were further increased in Alzheimer's disease, as determined by a study using functional magnetic resonance imaging (fMRI). The relationship between cerebral blood flow and the classical pathological hallmarks has been further supported by findings that amyloid beta is deposited on cerebral capillaries, termed Cerebral Amyloid Angiopathy (CAA), with over 80% prevalence in Alzheimer's disease. These studies further showed that vascular changes reduce amyloid beta clearance and that the amyloid beta preferentially builds up in areas whose cognitive functions are impaired in Alzheimer's disease.

While further research is determining the mechanisms by which cerebrovascular changes contribute to Alzheimer's disease, cerebral blood flow is an associated physiological marker of the disease. Furthermore, other types of neurocognitive disorders, including but not limited to vascular dementia or multi-infarct dementia, have been shown to demonstrate inadequate cerebral blood flow with an associated correlation between the degree of dementia and the cerebral blood flow itself.

Symptomology of Alzheimer's disease includes problems with various combinations of episodic memory, working memory, language, visuospatial ability, praxis and executive functions. These cognitive functions are supported by multiple brain areas working together in networks. However, brain areas and networks supporting other functions (such as early visual processing in the occipital lobe) are not primarily impaired in Alzheimer's disease. Therefore the neuropathology of Alzheimer's disease is dependent on differential activity, different blood flow patterns in different parts of the brain and the various anatomical changes progressing over time within the brain structure. Specifically, research has shown that Alzheimer's disease is associated with changes in prefrontal cortex in the frontal lobe, medial temporal areas in the temporal lobe and posterior parietal areas in the parietal lobe. These areas are part of the default mode network: the brain's activity when not performing a specific task (e.g. resting state), when daydreaming, when thinking about oneself, or other internally directed states. Multiple neuroimaging studies have shown that individuals with Alzheimer's disease have abnormal default mode network activity, involving medial temporal areas (e.g. hippocampal formation, entorhinal cortex), prefrontal cortex (e.g. ventromedial and dorsomedial prefrontal cortex), and posterior parietal cortex (e.g. temporal-parietal junction, inferior parietal lobule). The research shows reduced activity in as well as atrophy of the default mode network.

Changes in the default mode network have also been shown to occur before the occurrence or detection of amyloid plaque toxicity, supporting the efficacy of use of changes in the default mode network as an early marker of disease. Significant reductions in cerebral blood flow in the parietal lobule, angular gyrus and precuneus of mild cognitive impairment patients, measured using single-photon emission computed tomography (SPECT), has been shown to be predictive of their conversion to Alzheimer's disease. Alzheimer's disease also affects networks other than the default mode network, such as the network involved in verbal fluency (e.g. Broca's area, Wernicke's area and dorsolateral prefrontal cortex). These and other studies taken together suggest that Alzheimer's disease preferentially affects certain networks of brain areas, changing their activity as measured via blood flow, and that the patterns in network activity can distinguish Alzheimer's disease from healthy aging.

The described research has been generally performed utilizing functional magnetic resonance imaging (fMRI), positron emission tomography (PET) and single-photon emission computed tomography (SPECT). However, the machines used for such imaging are large and weigh thousands of kilograms, generally requiring a dedicated clinical room per unit, and in some cases the use of radioactive isotopes. The technical infrastructure, the significant budget to run and maintain such operations, the requirements for highly skilled technicians, the relatively low throughput of regular screening and the overall size and lack of portability of these solutions hinder the ability of medical practitioners worldwide to provide a frequent, rigorous and data-validated screening, monitoring and confirmation on the clinical diagnosis of Alzheimer's disease and its progression or other forms of dementia and their progression.

While these larger and more specialized clinical machines present the above limitations, new machine learning-based classification systems are now being considered to analyze brain network activity from data collected by these methods.

The present disclosure specifically offers an alternative approach to this cerebral data acquisition and data manipulation: 1) by using a portable and wireless acquisition device in the form of a medical grade helmet or headset with a series or arrays of multimodal sensors integrated at precise and pathologically-relevant locations within this particular form factor; and 2) by extracting cerebral data from one or multiple impaired and non-impaired cerebral regions at once thus allowing novelty assessments and continued monitoring on a per patient basis to be done more frequently, more economically at the primary care level in the vast majority of cases but also at the secondary care level in other cases, including but not limited to specialized clinics in some jurisdictions, in remote hospitals or in telemedicine scenarios, and this in all regions of the world, including the ones where functional magnetic resonance imaging (fMRI), positron emission tomography (PET) and single-photon emission computed tomography (SPECT) are not available or easily accessible for the vast majority of the local population due to significant costs, lack of advanced healthcare system, scarcity of highly trained medical specialists, nuclear or radioactive medicine technology importation bans, geographical remoteness, political restrictions, armed conflicts or various other localized factors.

FIG. 1 is a schematic drawing of a Portable Alzheimer's Disease Detection Device 1 with a Wireless Multimodal Sensor-based Headset 2 placed on top of a subject's head. The depicted Portable Alzheimer's Disease Detection Device 1 further comprises a wireless portable Computational Unit 3. As depicted in this exemplary embodiment, the Portable Alzheimer's Disease Detection Device 1 comprises two parts: the Wireless Multimodal Sensor-based Headset 2 and a wireless portable Computational Unit 3.

Figure 2:
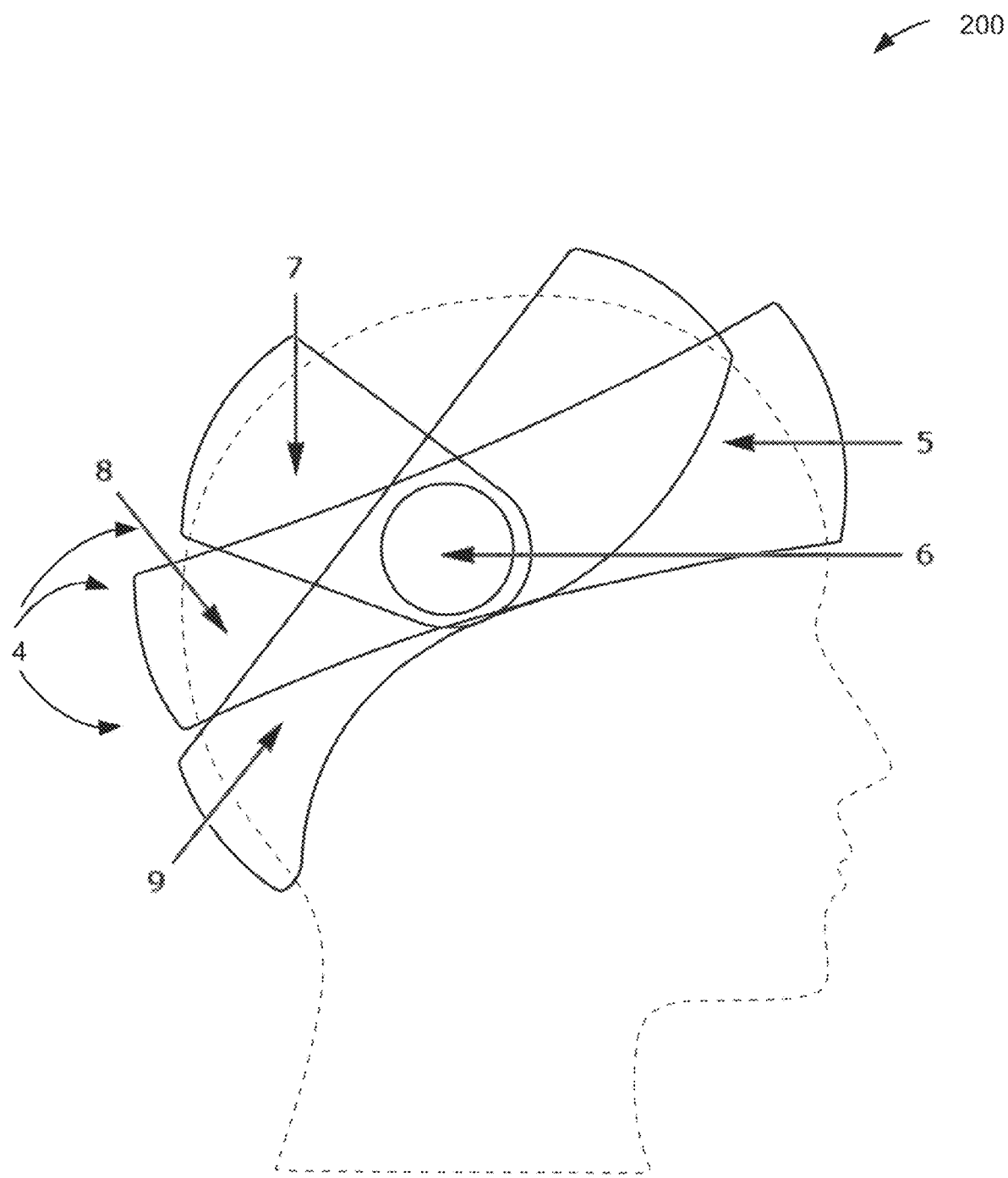

FIG. 2 is a schematic lateral projection of a Wireless Multimodal Sensor-based Headset 2 placed on top of a subject's head. FIG. 2 further depicts the three Flexible Resizable Elliptical Arms 4 and the following regions targeted for data acquisition and analysis: the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9.

As depicted in FIG. 2, the Wireless Multimodal Sensor-based Headset 2 may be a tri dimensionally-architectured headset composed of various sections including but not limited to three flexible resizable elliptical arms 4 that, when placed on a patient's head, may surround and provide functional access to or even touch the scalp directly above or on the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9.

Figure 3:
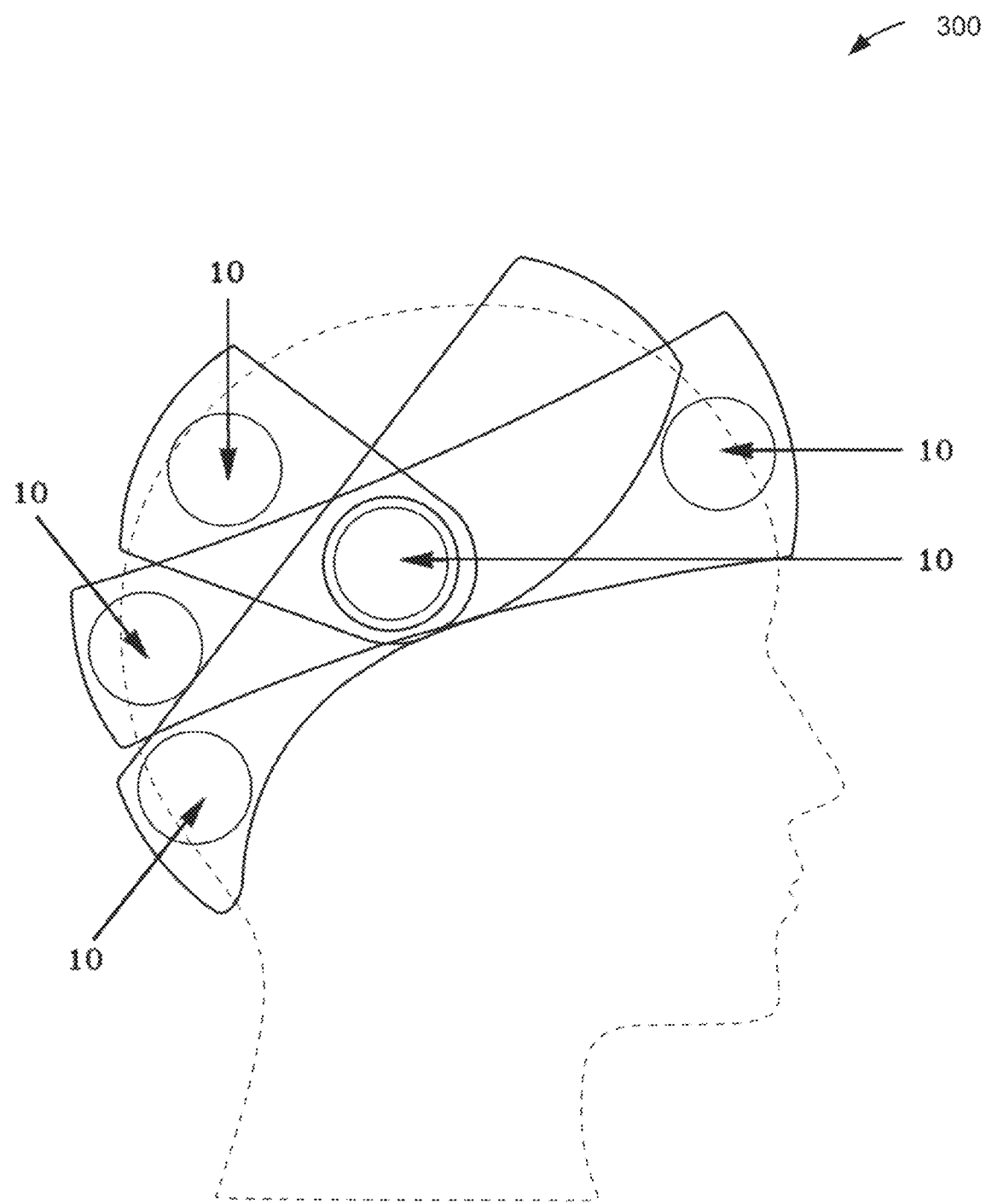
FIG. 3 is a schematic lateral projection of an example Wireless Multimodal Sensor-based Headset 2 placed on top of a subject's head according to some embodiments.

FIG. 3 is a schematic lateral projection of an example Wireless Multimodal Sensor-based Headset 2 placed on top of a subject's head. FIG. 3 shows three Flexible Resizable Elliptical Arms 4 with the multiple Multimodal Sensors 10 targeting the following regions for analysis: the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9.

It should be appreciated that although the terms "patient" and "subject" are used throughout this specification, the same concepts may apply more generally to any human being.

The Wireless Multimodal Sensor-based Headset 2 may be made of sufficiently-bendable lightweight medical grade materials to accommodate various sizes of human heads regardless of gender or age. The headset may also comprise a plurality of Multimodal Sensors 10 each targeting established craniological landmarks, specifically the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9.

Furthermore, in some embodiments the Multimodal Sensors 10 may be made of medical grade materials and designed to be easily removable, replaceable, and upgradeable. The Multimodal Sensors 10 may employ large circular shaped, screw-type electrical cable less contacts and coupling, which may be inserted and screwed within dedicated hole-shaped acoustically-isolating self-locking receptacles placed in specific positions on the three flexible resizable elliptical arms 4. This particular arrangement may enable the Multimodal Sensors 10 to be adjusted in order to place them at particular designated positions upon (and at a particular distance from) the patient's scalp, thereby enhancing the functionality of the Multimodal Sensors.

Additionally, the Wireless Multimodal Sensor-based Headset 2 may include but is not limited to a wirelessly-rechargeable, lockable, removable battery 11 located on one of the three flexible resizable elliptical arms 4. The Wireless Multimodal Sensor-based Headset 2 may also comprise various embedded electronic connecting circuitries 12 in the flexible resizable elliptical arms 4, which may allow self-powering autonomous activation upon the proper stereotactic positioning of the device on the patient's head, automatic sound and visual confirmations on each side of the three flexible resizable elliptical arms 4 upon the proper stereotactic positioning of the device on the patient's head, an automatic activation of date and time-based operations, an automatic time-based shut-off once the patient's assessment is deemed to be completed, as well as an analog-to-digital conversion chipset 13 and a data filtering and amplification chipset 14 to simultaneously collect data extracted by the Multimodal Sensors 10. The extracted data may then be transferred to the wireless portable Computational Unit 3. In some embodiments, the data transfer occurs upon the device's proper activation and at once via a Bluetooth-based chipset 15, which may be located on any of the three flexible resizable elliptical arms 4 and which allows traditional localized wireless secure computational pairing between the Wireless Multimodal Sensor-based Headset 2 and the Computational Unit 3.

In some embodiments, the Multimodal Sensors 10 may each comprise a single detachable, replaceable and easily upgradable form factor, a miniaturized flexible array of one or multiple functional near-infrared spectroscopy apparatus 16 and a miniaturized flexible array of one or multiple functional transcranial Doppler ultrasound apparatus 17, which can be used to simultaneously, or substantially simultaneously, detect, measure, collect and transmit measurements of key features such as cerebral oxygenation concentration and cerebral blood flow levels to a Cerebral Dataset 18.

It should be appreciated that this simultaneous multimodal technique via a Wireless Multimodal Sensor-based Headset 2 may be strictly architected for data acquisition in a programmed sequence for further data manipulation and data processing and not for traditional or experimental medical imaging purposes which are architected to produce images of objects or structures within a patient's anatomy.

Furthermore, this simultaneous multimodal technique via a Wireless Multimodal Sensor-based Headset 2 may not be architected for therapeutic application purposes, including but not limited to medical treatments for sonothrombolysis for ischemic stroke, stroke prophylaxis, intracranial hypertension, hydrocephalus or any other traditional or experimental therapeutic treatment of any neurological or vascular condition.

It should further be appreciated that this simultaneous multimodal data acquisition technique via a Wireless Multimodal Sensor-based Headset 2 may be a combination of data acquisition processes and may not intrinsically allow for an operational separation or processing separation between the functional near infrared spectroscopy apparatus 16 operating simultaneously with the transcranial Doppler ultrasound apparatus 17. Furthermore, the Multimodal Sensors 10 are to be considered as a single unitary component assembled either as a single medical micro-device component or single medical nano-device component in the Wireless Multimodal Sensor-based Headset 2 or as an array or arrays of single medical micro-device components or single medical nano-device components in the Wireless Multimodal Sensor-based Headset 2.

Figure 9:
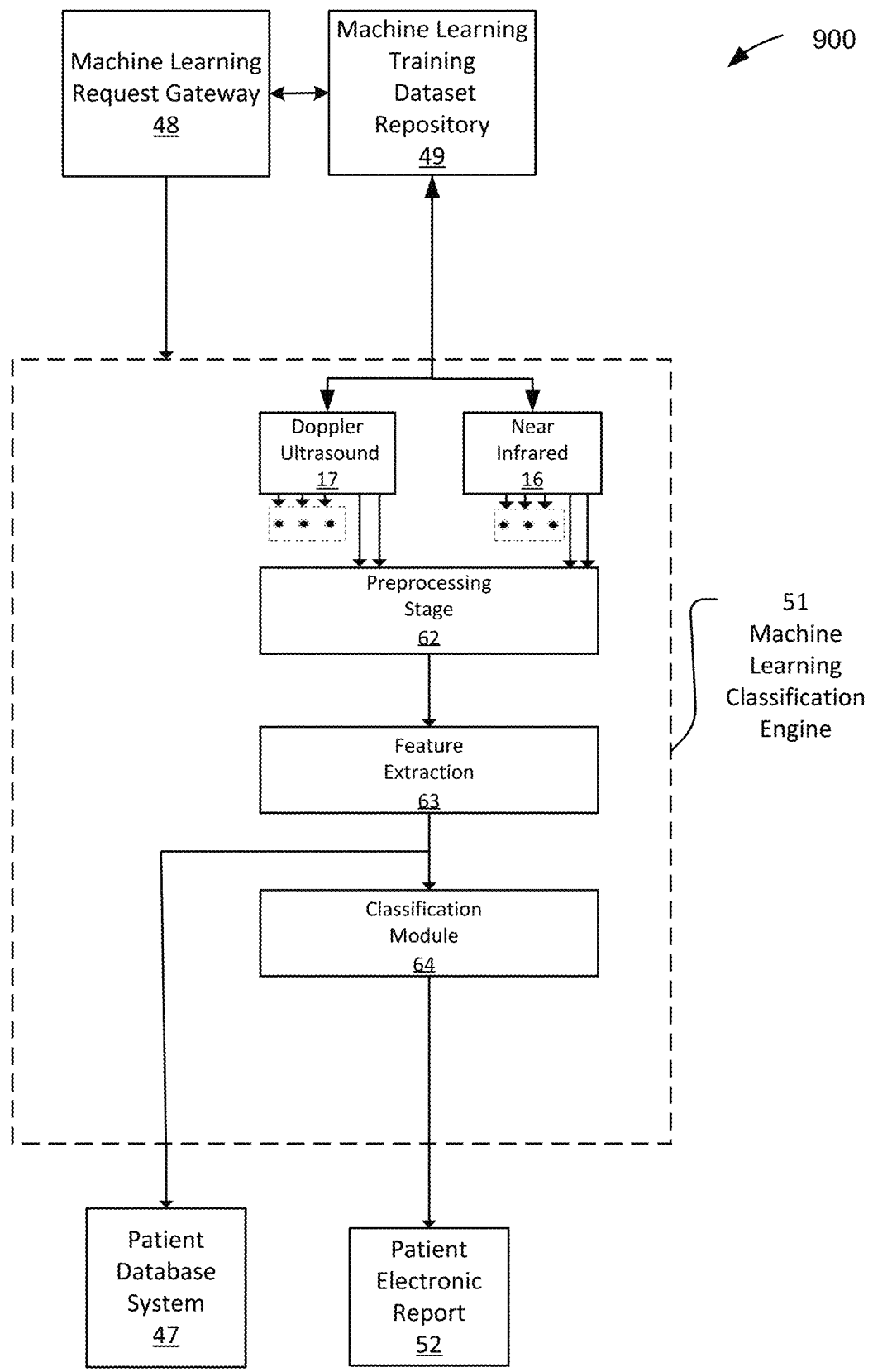
FIG. 9 is a flow diagram depicting an exemplary method for providing a machine learning process for analyzing Cerebral Datasets.

FIG. 9 is a flow diagram depicting a method by which the Machine Learning Classification Engine 51 processes one or more previously-archived Training Datasets 55 received from the Machine Learning Dataset Repository 49 in coordination with one or more Cerebral Datasets 18 produced by the Wireless Multimodal Sensor-based Headset 2 in order to determine the patient's pathological stage of Alzheimer's disease or another neurocognitive disorder.

In some embodiments, the Machine Learning Classification Engine 51 follows what is commonly known to persons of skill in the art as a "black box machine learning methodology". Specifically, as depicted in FIG. 9, a Preprocessing Stage 62 takes the raw signals from the Cerebral Dataset 18 acquired from the functional near infrared spectroscopy apparatus 16 operating simultaneously with the transcranial Doppler ultrasound apparatus 17, including but not limited to additional high-frequency micro-Doppler micro-ultrasound components, and filters the noisy signals by application of signal processing means in order to remove unwanted components or features ("noise").

In some embodiments, this filtering stage may apply one or more filters in time or frequency domains, including but not limited to finite impulse response, infinite impulse response, high-pass, low-pass, band-pass and all pass filters. Once filtered, the Machine Learning Classification Engine 51 may proceed to a Preprocessing Stage 62 which may provide output to feed the Classification Module 64.

In some embodiments, the Feature Extraction 63 stage may represent the preprocessed signal in a domain that allows the Classification Module 64 to better determine the diagnosis of patients. The Feature Extraction 63 output may include the same preprocessed signals, or a different representation of the signals based on operations including, but not limited to time-domain or frequency-domain. Furthermore, the Classification Module 64 may use the extracted features from the Feature Extraction 63 as input and its output may form, in part, the Patient Electronic Report 52.

The output may comprise a probabilistic predictive determination of the patient's diagnosis (a neurocognitive disorder detection score) as either a healthy control 26 or a subject with early mild cognitive impairment 27, late mild cognitive impairment 28 or Late Onset Alzheimer's disease 29 or a subject with a stage of a different neurocognitive disorder.

In some embodiments, the Classification Module 64 may be designed as supervised learning or unsupervised learning. In the supervised learning design, the algorithms may include, but are not limited to: Bayesian classifiers; non-parametric approaches such as density estimation and K-nearest Neighbor; linear discriminant analysis; neural networks, deep neural networks and non-metric methods such as decision trees. In the unsupervised learning design, the algorithms may include, but are not limited to: unsupervised Bayesian learning; clustering; and graph-theory methods.

In some embodiments, a single medical micro-device component or single medical nano-device component in the Wireless Multimodal Sensor-based Headset 2 or an array or arrays of single medical micro-device components or single medical nano-device components in the Wireless Multimodal Sensor-based Headset 2 may include a non-imaging non-invasive non-radioactive high-frequency micro-Doppler micro-ultrasound architecture able to detect in vivo blood flow variations at the molecular level in various sections of the studied regions, such raw data being additionally extracted in real-time in combination with the raw data extracted from the other data acquisition apparatus for simultaneous micro-cerebrovascular and macro-cerebrovascular functional assessments. This may allow machine-learning classification and predictive modelling to be defined from twenty or more simultaneous multimodal input sources extracting raw data from five specific craniological regions of the brain at once as herein described.

In some embodiments, to perform the data collection, the Wireless Multimodal Sensor-based Headset 2 is placed on the patient's head, as if wearing a helmet. The extraction of the Cerebral Dataset 18 may then be conducted by the device and transmitted to the wireless portable Computational Unit 3 for further data processing, analysis, reporting and storage as described herein.

In some embodiments, each of the Multimodal Sensors 10 may include, but are not limited to, a combination of sealed miniaturized laser light-emitting diodes 19, which may provide an amplitude-modulated sinusoidal frequency spectrum 20 projected inside of fiber-optic cable arrays 21, which may allow the emission of light onto the surface of the patient's cranium, such fiber-optic cable arrays 21 being configured to produce one or more combined patterning methods, including but not limited to regular linear patterning, curved linear patterning, multichannel grouped patterning, two-dimensional grid-like patterning, toothbrush-like patterning or random patterning. Changes in the backscattered signal's amplitude and phase may be instantaneously detected, measured, and/or captured via optically-sensitive detectors 22 to provide information on time-based changes in key features such as the concentration of hemoglobin and cerebral oxygenation, and to provide a direct measurement of absorption coefficients.

In some embodiments, each of the multimodal sensors 10 may include, but are not limited to, sealed, miniaturized, functional transcranial Doppler ultrasound transducer probes 23. The probes 23 emit inaudible high-frequency acoustic waves 24 and detect changes in pitch between the emitted high-frequency acoustic waves 24 and detected reflections of same in order to measure the velocity of cranial blood flow through the brain's blood vessels over time. This measurement, when processed according to the methods described herein, may allow for acquisition of cerebral blood flow levels from the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9.

In some embodiments, once the above data collection is initiated, the Computational Unit 3 may analyze the patient's Cerebral Dataset 18 against on or more cloud-based historical data collection samplings 25 from other patients or subjects. The historical data collection samplings 25 may be obtained from other patients exhibiting healthy brain activity which can be used as healthy controls 26. The samplings 25 may also be obtained from one or more of: subjects previously diagnosed with early mild cognitive impairment 27; subjects previously diagnosed with late mild cognitive impairment 28; subjects previously diagnosed with Late Onset Alzheimer's disease 29; or subjects previously diagnosed with other types and other stages of neurocognitive disorders.

In some embodiments, the analysis of the patient's Cerebral Dataset 18 against the historical data samplings 25 may be carried out via built-in machine learning classifiers 30 and further predictive mathematical algorithms 31 to determine the patient's pathological stage of Alzheimer's disease or of a different neurocognitive disorder.

In some embodiments, the machine-learning classifiers 30 may filter, isolate and label the assessed patient as having Alzheimer's versus other kinds of neurocognitive disorders and the predictive mathematical algorithms 31 may process data comprising historical patterns from the Training Dataset 55 to further predict the pathological stage or progression over time of the classified disease.

In some embodiments, the newly-acquired measurement levels of both cerebral blood flow and cerebral oxygen concentration may also be processed to generate visual representations of both the real-time reporting against historical reporting for the patient 33 and the display of the clinical variance analysis over time which may provide means to track the evolution of the Alzheimer's Disease or of a different neurocognitive disorder 32 over time.

Figure 4:
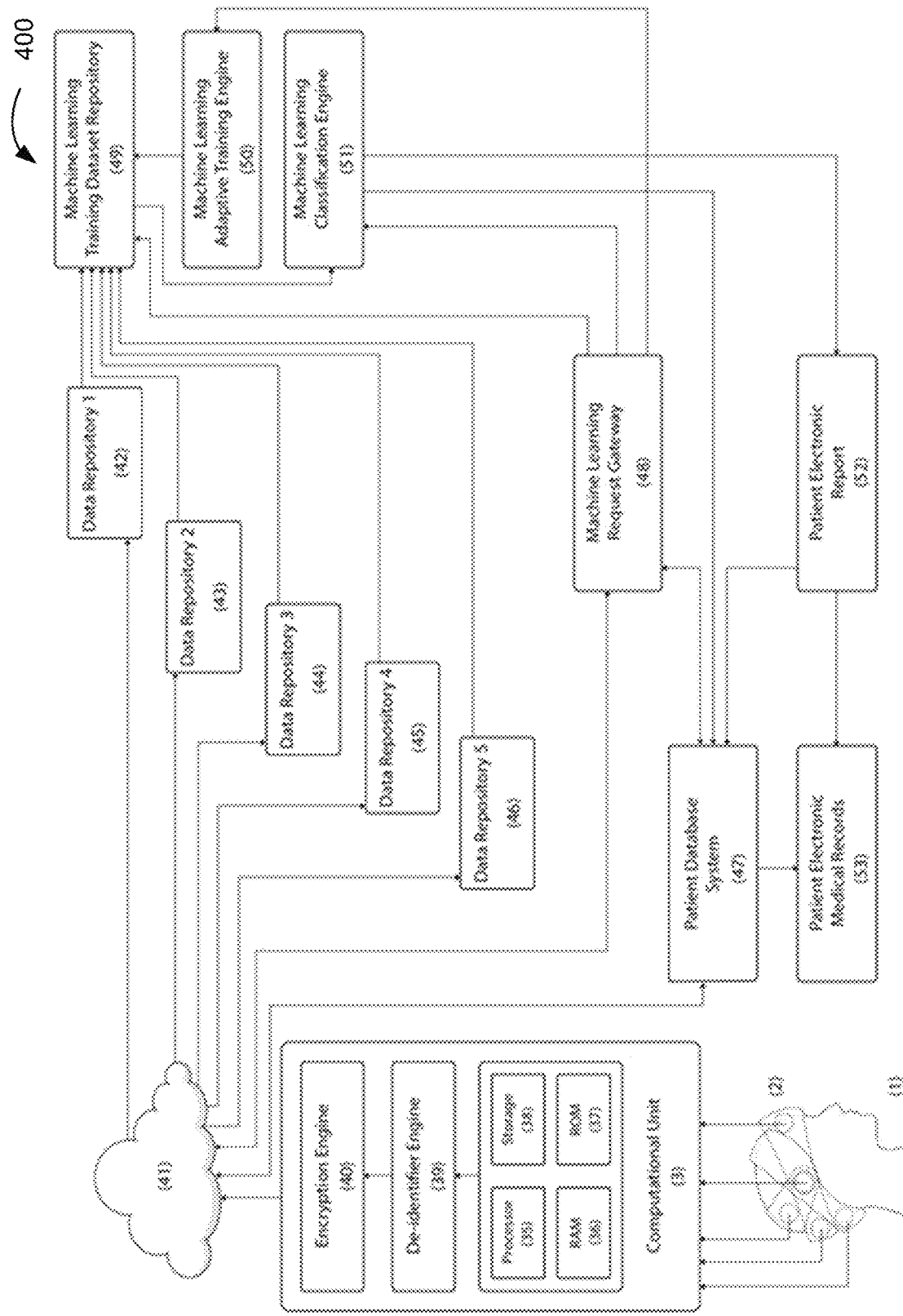
FIG. 4 is a flow diagram depicting the patient cerebral data processing workflow according to some embodiments.

FIG. 4 is a flow diagram depicting the patient cerebral data processing workflow according to some embodiments of the present disclosure. FIG. 4 presents the analytical logic, computation processes and data management procedures of the Portable Alzheimer's Disease Detection Device 1 according to an embodiment.

In some embodiments, the sensorial locations defined as the Frontal Regions of the Human Brain 5, the Temporal Regions of the Human Brain 6, the Parietal Regions of the Human Brain 7, the Occipital Regions of the Human Brain 8 and the Cerebellar Regions of the Human Brain 9 may be the source of simultaneous Cerebral Dataset 18 acquisitions via the Wireless Multimodal Sensor-based Headset 2. Such cerebral information is unprocessed, non-classified raw data which may be transmitted live via a Bluetooth-based chipset 15 (or via other data communication means) to the Computational Unit 3.

In some embodiments, the Computational Unit 3 may be a computer hardware device, such as a tablet computer or a laptop computer or any embedded computer system with at minimum a central processor unit 35, random access memory, commonly referred to as 'RAM' 36, read-only memory, commonly referred to as 'ROM' 37, and non-volatile storage memory, commonly referred to as a computer hard drive or flash memory storage. The Computational Unit 3 may function as a standard computer with a standard computer operating system able to run independent software applications, and executed pre-programmed instructions.

In some embodiments, upon receiving the unprocessed non-classified raw Cerebral Dataset 18, for example wirelessly via the Bluetooth protocol or via another data communication protocol, the Computational Unit 3 de-identifies the Cerebral Dataset 18 from that specific patient for optimal confidentiality, security and privacy via a local De-identifier Engine 39 anonymizing the received information such that no traceable contact identification of any kind may remain to associate said received information with the patient. Upon successful completion of the de-identification process, a secondary technique may be applied which may automatically encrypt the de-identified information according to commercially-available military grade encryption methodology embedded in a local Encryption Engine 40 which may also be installed on the Computational Unit 3. Once completed, the Cerebral Dataset 18 may then be forwarded electronically (e.g., via the secure file transfer protocol (SFTP)) to a Remote Storage Device 42-46.

In some embodiments, the Remote Storage Device 42-46 may be a secure geo-located data center-based computer server architecture, which has been identified by the Computational Unit 3 and the Encryption Engine 40 as a technically available recipient for the Cerebral Dataset 18 based on various factors. These factors may include, for example, the geographical location of the data acquisition itself (e.g., via GPS-based technology or IP geolocation analysis done by the Computational Unit 3 and the Encryption Engine 40).

In some embodiments, the Remote Storage Device 42-46 may be confirmed as available and valid geographically speaking via a first electronic confirmation issued by the Machine Learning Request Gateway 48 monitoring, authorizing or declining all processing requests from the Computational Unit 3 and the Encryption Engine 40 as per pre-installed and remotely updatable computation rules. These pre-installed, remotely updatable computation rules may be based on the legal and/or regulatory requirements within the Local Legal Geographical Jurisdiction regarding medical records, patients' data storage and patients' data manipulation 58.

In some embodiments, transfer of the Cerebral Dataset 18 may only be initiated once the Machine Learning Request Gateway 48 has confirmed a match between the geo-location of the provenance of the Cerebral Dataset 18 and at least one technically available and legally authorized geo-located Remote Storage Device 42-46. Once a match is found, the Computational Unit 3 and the Encryption Engine 40 may issue a serialized software token authorization key validation process 54 for the transfer of the Cerebral Dataset 18 to proceed and a log may be updated to include a record of the transfer request and the serialized software token authorization key validation process 54 in a separate Patient Database System 47.

In some embodiments, the serialized software token authorization key validation process 54 may be unique to each patient's Cerebral Dataset 18 and may be composed at a minimum of the cryptographic formulation of cipher text including one or more of the geolocation information, date, time and embedded chipset information from the Computational Unit 3 and the Wireless Multimodal Sensor-based Headset 2. Upon the successful transfer of the de-identified encrypted Cerebral Dataset 18 to the approved Remote Storage Device 42-26, an identical copy of the de-identified encrypted Cerebral Dataset 18 may be transferred to the Machine Learning Training Dataset Repository 49 and the Machine Learning Request Gateway 48 may release a copy of the serialized software token authorization key validation process 54 to the Machine Learning Training Dataset Repository 49 and to the Machine Learning Classification Engine 51.

In some embodiments, the Machine Learning Training Dataset Repository 49 may then confirm a unique match from the serialized software token authorization key validation process 54 and may allow the Machine Learning Classification Engine 51 to decrypt the Cerebral Dataset 18 and filter and classify, via Machine Learning Classifiers 30 and Predictive Mathematical Algorithms 31, the decrypted and de-identified Cerebral Dataset 18 against the previously-archived Training Dataset 55 of the Machine Learning Dataset Repository 49 to determine the patient's pathological stage of Alzheimer's disease or of a different neurocognitive disorder based on key features such as levels of both cerebral blood flow and cerebral oxygen concentration from one or more of: the patient's Frontal Regions of the Human Brain 5; the Temporal Regions of the Human Brain 6; the Parietal Regions of the Human Brain 7; the Occipital Regions of the Human Brain 8; and the Cerebellar Regions of the Human Brain 9, as detected and acquired by the Wireless Multimodal Sensor-based Headset 2. Upon successful classification, the Machine Learning Classification Engine 51 may create an electronic Patient Electronic Report 52 comprising the results from the above assessment and/or a probabilistic determination of the patient's diagnosis (a neurocognitive disorder detection score) as either a healthy control 26 or a subject with early mild cognitive impairment 27, late mild cognitive impairment 28 or Late Onset Alzheimer's disease 29 or a subject with a stage of a different neurocognitive disorder. According to some embodiments, this report may be technically compatible with applicable government-regulated third-party systems for the management and storage of Patient Electronic Medical Records (53).

In some embodiments, the Machine Learning Classification Engine 51 may also issue a Digital Analytical Biomarker 56 comprising a data-only version of the Patient Electronic Report 52 and a copy of the serialized software token authorization key validation process 54. The Digital Analytical Biomarker 56 may then be forwarded to the Patient Database System 47, at which point the originally-submitted serialized software token authorization key validation process 54 stored in the Patient Database System 47 may be instantly (or rapidly) matched with the Digital Analytical Biomarker 56 allowing for a secure government-regulated application programming interface (API)-based transfer of the Patient Electronic Report 52 including the neurocognitive disorder detection score into the third-party system for Patient Electronic Medical Records 53, such transfer accessing and locating in the Patient Electronic Medical Records 53 an internationally-approved procedural unique healthcare alphanumeric code associated with that type of diagnostic exam and further associated with that patient, the date and time of the diagnostic exam and a unique device serialization value strictly allocated to the registered Licensed Device-Certified Medical Doctor 57.

In some embodiments, once the transfer of the Patient Electronic Report 52 is completed, the Patient Database System 47 may be updated and may immediately cause to expire, cancel and render useless the authorization keys in the previously-issued serialized software token authorization key validation process 54 in the Machine Learning Request Gateway 48, which itself may then propagate that cancellation in the Machine Learning Training Dataset Repository 49 and the Machine Learning Classification Engine 51. This may prohibit any further activation for classification processing on the acquired Cerebral Dataset 18. The Machine Learning Request Gateway 48 may (in some embodiments this may occur substantially simultaneously or substantially simultaneously with the propagation of the above-mentioned cancellation in the Machine learning Training Dataset Repository 49) issue a computing batch command for the Machine Learning Adaptive Training Engine 50 to immediately generate the permanent transfer of the decrypted and de-identified Cerebral Dataset 18 still residing in the Machine Learning Training Dataset Repository 49 into the historical Training Dataset 55 of the Machine Learning Dataset Repository 49, as a new statistical sample in the historical Training Dataset 55, such insertion taking place based on a prioritization analysis of the Central Processing Unit usage, commonly referred to as CPU usage, the running computer services associated with the Machine Learning Training Dataset Repository 49 and an electronic confirmation issued by the patient via the Computational Unit 3 And an electronic confirmation for a Cerebral Dataset Security Scan Verification 60 issued by the Machine Learning Request Gateway 48.

In some embodiments, the Cerebral Dataset Security Scan Verification 60 may be tailored to immediately inject a Cerebral Dataset Sample Signature 61, the specific role of which is to authenticate and validate any further use of that specific patient's sample in the Historical Training Dataset 55, into the finalized Cerebral Dataset 18 ready for integration in the Historical Training Dataset 55. Furthermore, the Cerebral Dataset Security Scan Verification 60 may change the read/write property of the Cerebral Dataset 18 to 'read-only' once the injection of the Cerebral Dataset Sample Signature 61 is completed. Without this unique and time-based Cerebral Dataset Sample Signature 61 based on the registered device information and the patient's finalized multimodal Cerebral Dataset acquisition, that sample cannot be considered as being a valid sample and as internally-generated by the said architecture and the said registered device.

In some embodiments, this hardware-software sealing data protection measure transforms the previously-de-identified and decrypted Cerebral Dataset 18 immediately from one specific dataset architecture into another. This may produce a new non-writable "enveloped" dataset architecture specifically preventing, at the creation point of the Cerebral Dataset 18 any transfer into a Historical Training Dataset 55 any potential malicious data modification or unauthorized data substitution via malware or any other data-driven synthetic adversary input or external vulnerability, which would now be technically and analytically disregarded in any filtering, classification or predictive processing if such attack on that sample would be attempted.

In some embodiments, the Machine Learning Training Dataset Repository 49 is tailored to constantly verify upon each new Cerebral Dataset 18 addition in the Historical Training Dataset 55 that the new addition, as well as each and every sample in the Historical training set 55, has been transformed according to the Cerebral Dataset Security Scan Verification 60 and into the secure format carrying the Cerebral Dataset Sample Signature 61.

In some embodiments, if one Cerebral Dataset 18 is present in the Historical Training Dataset 55 without a Cerebral Dataset Sample Signature 61 formatted pattern, the Machine Learning Training Dataset Repository 49 immediately may flag the sample, render it as a non-valid sample, and may log the protective intervention in the Patient Database System 47. Further, this may cause immediate notification of the IT services or Administrator in charge of the said architecture. In some embodiments, if more than one sample in the Historical Training Dataset 55 is found to be without a Cerebral Dataset Sample Signature 61 upon such verification, the Machine Learning Training Dataset Repository may be immediately rendered as non-available for further processing and may log the protective intervention in the Patient Database System 47. The Patient Database System 47 may be configured to immediately notify the IT services or Administrator in charge of the said architecture.

In some embodiments, whereas the Local Legal Geographical Jurisdiction overseeing medical records, patients' data storage and patients' data manipulation 58 and the Local Laws and regulations regulating medical records, patients' data storage and patients' data manipulation 59 may provide the patients with specific data subject rights including right to access, data portability and right to be forgotten, the hereinabove described processing may further include an immediate transfer of the Patient Electronic Report 52 from the Patient Database System 47 into the Computational Unit 3 in a standard governmentally-accepted computer format, such as an Adobe .PDF format and/or a Comma-Separated Value format also referred to as .CSV, for the Patient to review and allow for manipulation including, but not limited to, printing, emailing or further third-party data importing for regulatory compliance. The digital notification for local access to the Patient Electronic Report 52 on the Computational Unit 3 may be accompanied by a single statement requesting formal consent (e.g., click-wrap consent) from the patient for the insertion of the patient's analytical results from the assessment to be stored as a decrypted de-identified statistical sample in the Machine Learning Training Dataset Repository 49. In a case of refusal, the Computational Unit 3 may immediately notify the Machine Learning Request Gateway 48, which itself may cause the refusal to be logged in the Patient Database System 47, and the Cerebral Dataset 18 may then be automatically and permanently deleted from the Remote Storage Device 42-46 and/or the Machine Learning Training Dataset Repository 49. Confirmation (e.g., visual or audio confirmation via a user interface device such as display of the Computational Unit 3) may be provided upon completion, and an automated log entry in the Patient Electronic Medical Records 53 may be created.

Figure 5:
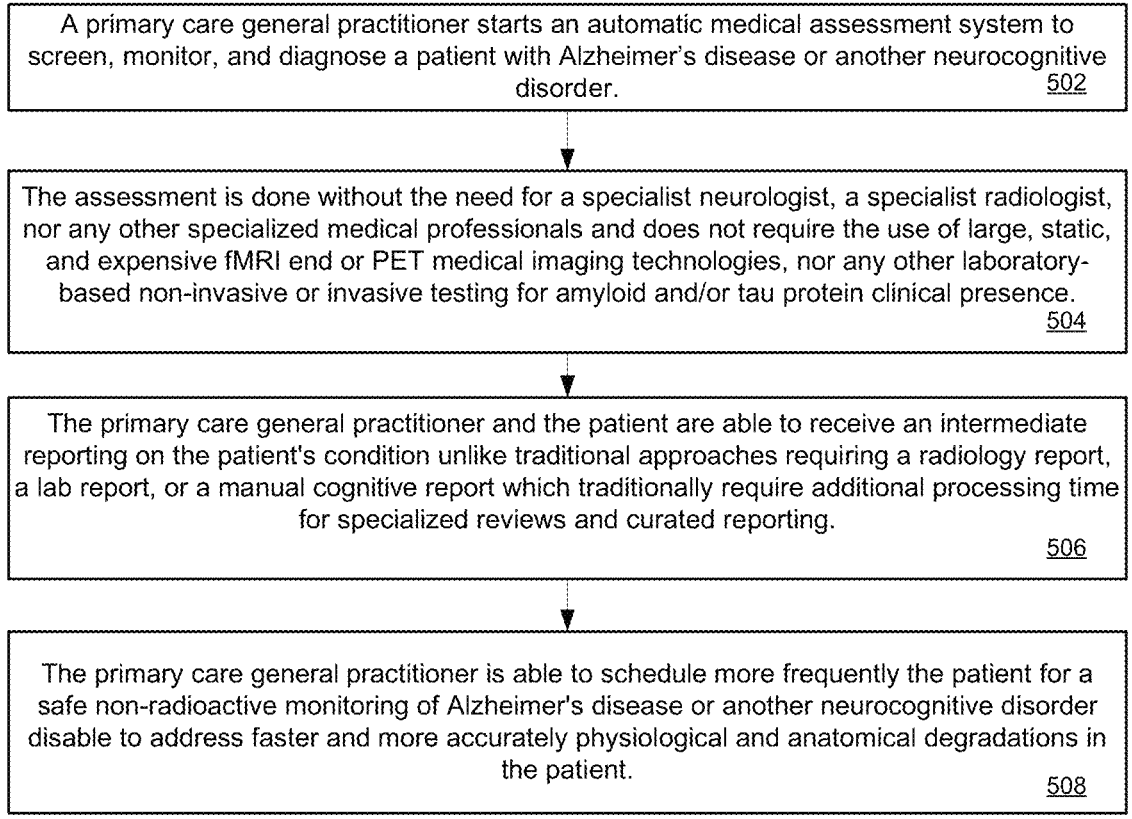
FIG. 5 is a flow diagram depicting a method for screening individuals for Alzheimer's disease or other neurocognitive disorders.

FIG. 5 depicts a method for screening individuals for Alzheimer's disease or other neurocognitive disorders according to an embodiment. At 502, a primary care general practitioner starts an automatic medical assessment system to screen, monitor, and diagnose a patient with a neurocognitive disorder such as Alzheimer's disease.

At 504, the assessment is conducted without the need for the intervention of a specialist neurologist, a specialist radiologist, nor any other specialized medical professionals and does not require the use of large static and expensive fMRI and/or PET medical imaging technologies nor any other laboratory-based non-invasive or invasive testing for amyloid and/or tau protein clinical presence.

At 506, the primary care general practitioner and the patient are able to receive an immediate reporting on the patient's condition, unlike traditional approaches which require a radiology report, a lab report, or a manual cognitive report. Traditional approaches traditionally require additional processing time for specialized reviews and curated reporting.

At 508, the primary care general practitioner is able to schedule patients more frequently for a safe non-radioactive monitoring of Alzheimer's disease or other neurocognitive disorders, thus enabling them to trace and quickly address physical and anatomical degradations in patients.

Figure 6:
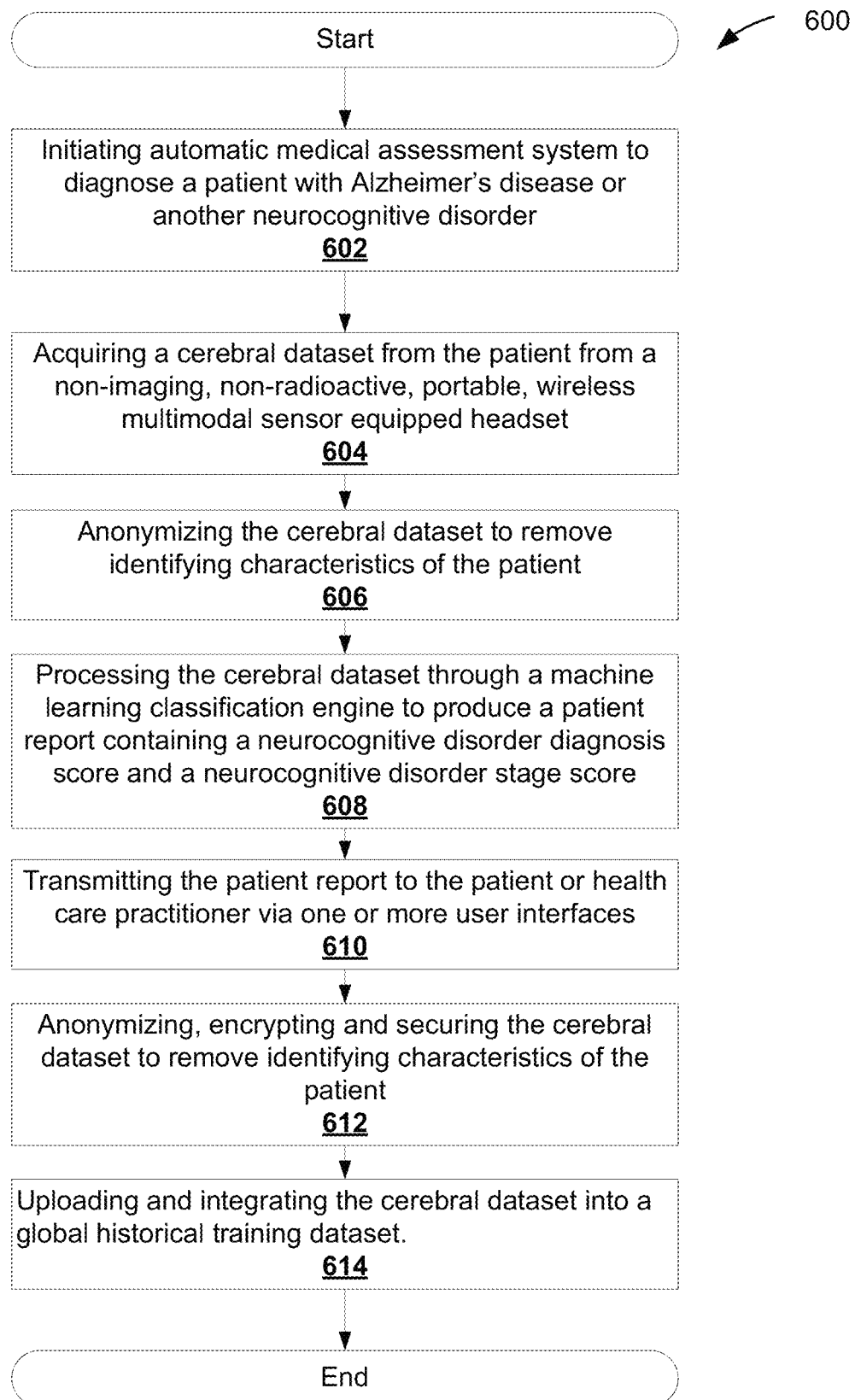
FIG. 6 is a flow diagram depicting a method for providing a system for classification of patients with Alzheimer's disease or other neurocognitive disorders based on the progression of the disease over time.

FIG. 6 is a flow diagram depicting a method for providing a system for classification of patients with Alzheimer's disease or other neurocognitive disorders based on the progression of the disease over time. At 602 an automatic medical assessment system to diagnose a patient with Alzheimer's disease or another neurocognitive disorder is initiated. At 604 a cerebral dataset is acquired from the patient via a non-imaging, non-radioactive, portable, wireless multimodal sensor equipped headset. At 606, the cerebral dataset is anonymized to remove identifying characteristics of the patient. At 608, the cerebral dataset is processed through a machine learning classification engine to produce a patient report containing a neurocognitive disorder diagnosis score and a neurocognitive disorder stage score. At 610, the patient report is transmitted to the patient and/or health care practitioner via one or more user interfaces. At 612, the patient report is put through a process which includes anonymizing, encrypting and/or securing the cerebral dataset to remove identifying characteristics of the patient. At 614, the patient report is uploaded and integrated into a global historical training dataset.

Figure 7:
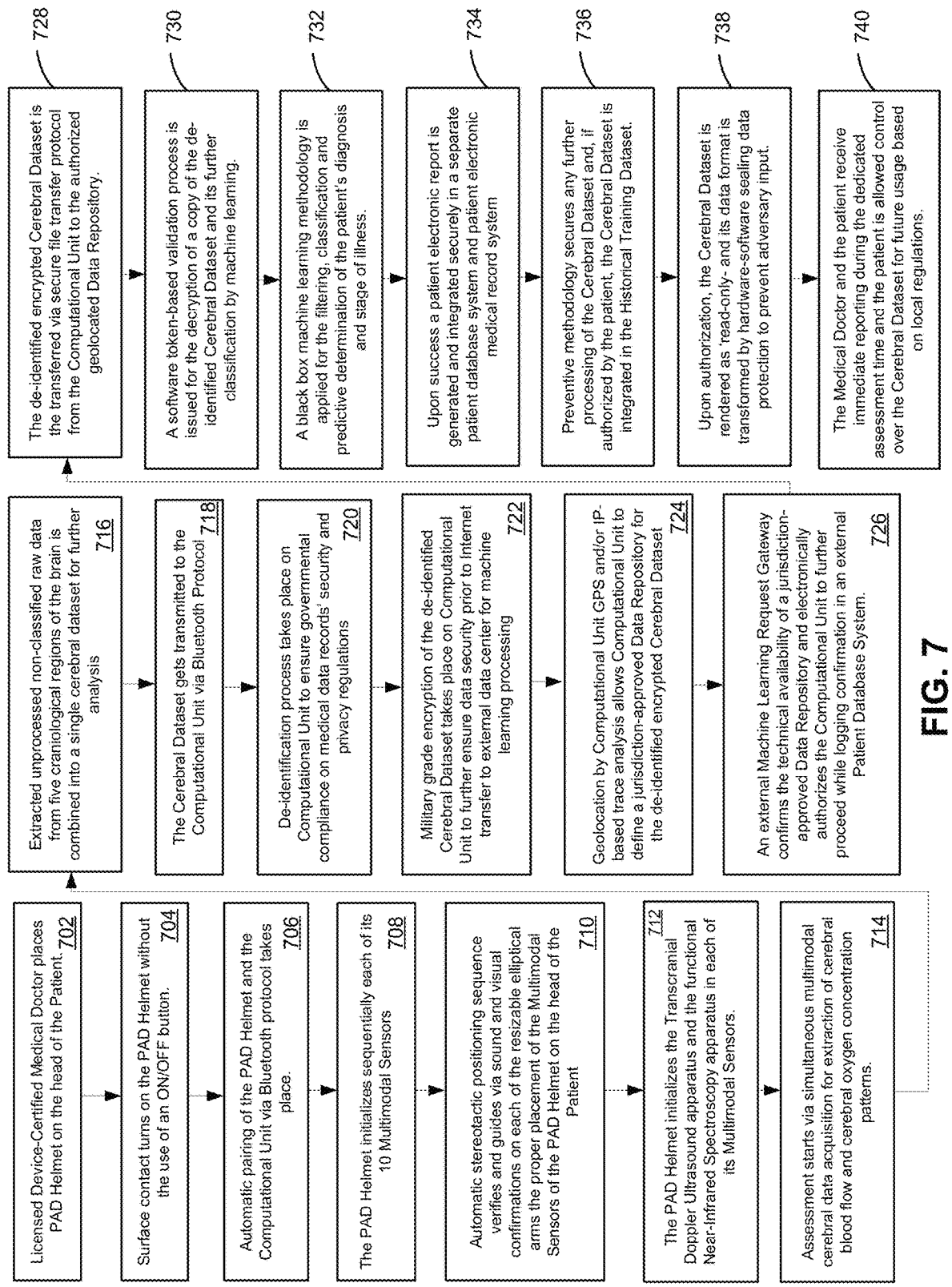
FIG. 7 is a flow diagram depicting operational steps in an exemplary method of providing a system for classification of patients with Alzheimer's disease or other neurocognitive disorders based on the progression of the disease over time.

FIG. 7 is a flow diagram depicting operational steps in an exemplary method of providing a system for classification of patients with Alzheimer's disease or other neurocognitive disorders based on the progression of the disease over time. At 702 a licensed device-certified medical doctor places helmet on the head of the patient. At 704 surface contact turns on the helmet without the use of an on-off button. At 706, Automatic pairing of the helmet and the computational unit via Bluetooth protocol takes place. At 708, The helmet initializes sequentially each of its 10 multi-modal sensors. At 710, automatic stereotactic positioning sequence verifies and guides, via sound and visual confirmations, the proper placement of each of the resizable elliptical arms of the multimodal sensors of the helmet on the head of the patient. At 712, the helmet initializes the transcranial Doppler ultrasound apparatus and the functional near-infrared spectroscopy apparatus in each of its multimodal sensors. At 714, Assessment starts via simultaneous multimodal cerebral data acquisition for extraction of cerebral blood flow and cerebral oxygen concentration patterns. At 716, extracted unprocessed non-classified raw data from the five craniological regions of the brain is combined into a single cerebral dataset for further analysis. At 718, the cerebral dataset gets transmitted to the computational unit via Bluetooth protocol, or another data transfer protocol. At 720, de-identification process takes place on computational unit to ensure governmental compliance on medical data records security and privacy regulations. At 722, military grade encryption of the De-identified cerebral dataset takes place on computational unit to further ensure data security prior to the internet transfer to external data center for machine learning processing. At 724, geolocation by computational unit GPS and or ip-based Trace analysis allows computational unit to define a jurisdiction-approved data repository for the de-identified encrypted cerebral dataset. At 726, an external machine learning request Gateway confirms the technical availability of a jurisdiction-approved data repository and electronically authorizes the computational unit to further proceed while logging the confirmation in an external patient database system. At 728, the de-identified encrypted cerebral dataset is then transferred via secure file transfer protocol from the computational unit to the authorized geo-located data Repository. At 730, a software token based validation process is issued for the decryption of a copy of the de-identified cerebral dataset and it's further classification by machine learning. At 732, a black box machine learning methodology is applied for the filtering, classification, and predictive determination of the patient's diagnosis and stage of illness. At 734, upon success, a patient electronic report is generated and integrated securely in a separate patient database system and patient electronic medical record system. At 736, Preventative methodology secures any further processing of the cerebral dataset and, if authorized by the patient, the cerebral dataset is integrated in the historical training dataset. At 738, upon authorization, the cerebral dataset is rendered as read only and its data format is transformed by hardware-software sealing data protection to prevent adversary input. At 740, the medical doctor and the patient receive immediate reporting during the dedicated assessment time and the patient is allowed control over the cerebral dataset for future usage based on local regulations.

Figure 8:
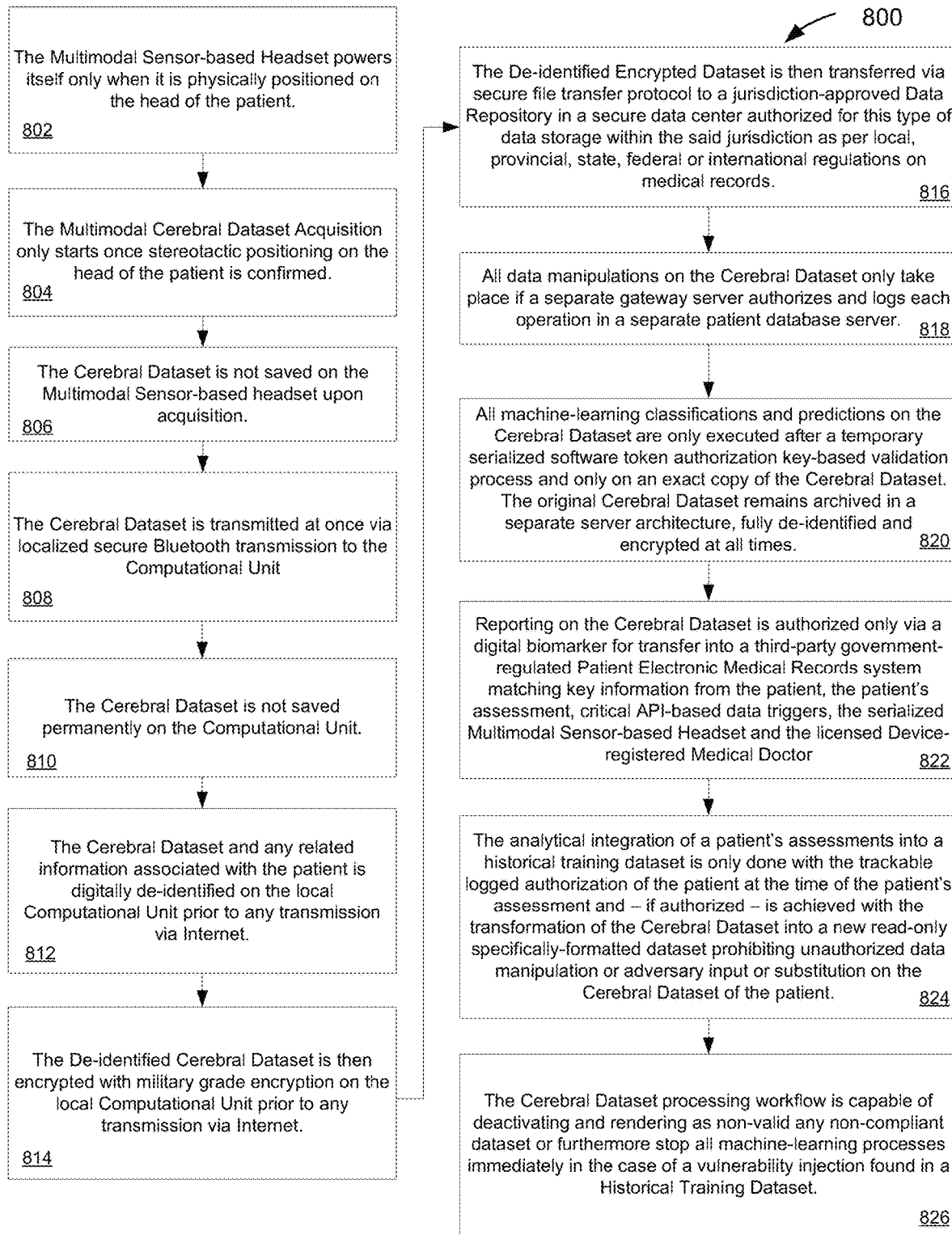
FIG. 8 is a flow diagram depicting an exemplary Cerebral Data security protocol and process.

FIG. 8 is a flow diagram depicting an exemplary Cerebral Data security protocol and process. At 802, the multimodal center based headset powers itself only when it is physically positioned on the head of the patient. At 804, the multimodal cerebral dataset acquisition only starts once stereotactic positioning on the head of the patient is confirmed. At 806, the cerebral dataset is not saved on the multimodal sensor-based headset upon acquisition. At 808, the cerebral dataset is transmitted at once via Bluetooth transmission to the computational unit. At 810, cerebral dataset is not saved permanently on the computational unit. At 812, the cerebral dataset and any related information associated with the patient is digitally de-identified on the local computational unit prior to any transmission via internet. At 814, the de-identified, encrypted dataset is then transferred via secure file transfer protocol to a jurisdiction-approved data repository in a secure data center authorized for this type of data storage within the said jurisdiction as per applicable laws and regulations. At 816, all data manipulations on the cerebral dataset only take place if a separate gateway server authorizes and logs each operation in a separate patient database server. At 818, all machine-learning classifications and predictions on the cerebral dataset are only executed after a temporary serialized software token authorization key-based validation process and only on an exact copy of the cerebral dataset. The original cerebral dataset remains archived in a separate server architecture, fully anonymized and encrypted at all times. At 820, reporting on the cerebral dataset is authorized only via a digital biomarker for transfer into a third-party government-regulated patient electronic medical record system matching key information from the patient, the patient assessment, critical API-based data triggers, the serialized multimodal sensor based headset, and the licensed device registered medical doctor. At 822, the analytical integration of a patient assessment into historical training dataset is only done with the trackable logged authorization of the patient at the time of the patient's assessment and if authorized is achieved with the transformation of the cerebral dataset into a new read-only formatted dataset prohibiting unauthorized data manipulation or adversary input or substitution on the cerebral dataset. At 824, the cerebral dataset processing workflow is capable of deactivating and rendering as non-valid any non-compliant dataset, or furthermore stopping all machine learning processes immediately in the case of a vulnerability injection found in historical training dataset.

Figure 10:
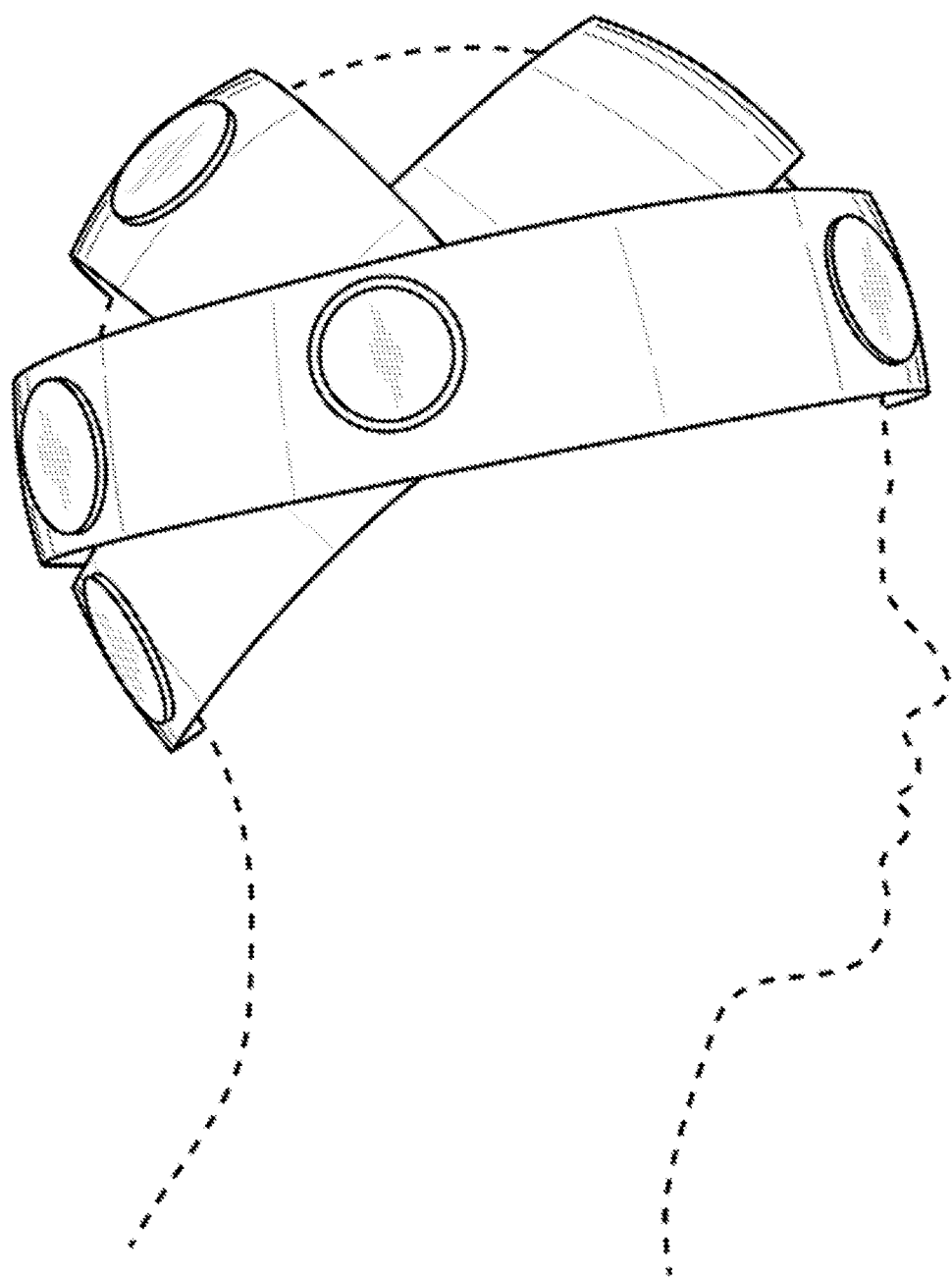
FIG. 10 is a side view of an example wireless multimodal sensor-based headset atop the head of a subject.

FIG. 10 is a side view of an example wireless multimodal sensor-based headset atop the head of a subject.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more sensory output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references may be made regarding servers, services, interfaces, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The embodiments described herein are also implemented by physical hardware, including computing devices, sensory devices, servers, receivers, transmitters, processors, memory, displays, and networks. The embodiments described herein provide useful physical machines and particularly configured computer hardware arrangements.

The embodiments described herein are also directed to electronic machines and methods implemented by electronic machines adapted for processing and transforming signals which represent various types of information. The embodiments described herein pervasively and integrally relate to machines, and their uses; and the embodiments described herein have no meaning or practical applicability outside their use with hardware, machines, and various hardware components.

Substituting the physical hardware particularly configured to implement various acts for non-physical hardware, using mental steps for example, may substantially affect the way the embodiments work. Such hardware limitations are clearly essential elements of the embodiments described herein, and they cannot be omitted or substituted for mental means without having a material effect on the operation and structure of the embodiments described herein. The hardware is essential to implement the various embodiments described herein and is not merely used to perform steps expeditiously and in an efficient manner. In some embodiments, the device is a single or special purpose machine that is specifically designed to perform limited set of functionality.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized.

As can be understood, the examples described above and illustrated are intended to be exemplary only.

All documents cited herein are incorporated into the present disclosure in their entirety by reference.

REFERENCES

The following are hereby incorporated in their entirety by this reference.

Patents

U.S. Pat. No. 9,367,817 B2; U.S.14115781; U.S. 20150046176 A1; U.S. 20120083718 A1; U.S. 20070232918 A1; U.S.20060099624; U.S.20040049105 A1; U.S.20110251489 A1; U.S.20020095087 A1; U.S.20020095087 A1; U.S. 09995897; U.S. Pat. Nos. 6,875, 176; 5,946,647 A.

Non-Patent Literature

Evans A. et al. McGill University Newsroom, 2016 "Big Data study discovers earliest sign of Alzheimer's".

van de Haar H. et al Neurobiology of Aging, Online Publication, No. 2016.06.006, 2016 "Neurovascular unit impairment in early Alzheimer's disease measured with magnetic resonance imaging".

Perrotta M. et al. International Journal of Molecular Sciences, Vol. 17, No. 3, p. 347, 2016 "Hypertension and Dementia: Epidemiological and Experimental Evidence Revealing a Detrimental Relationship".

Alberdi A. et al. Artificial Intelligence in Medicine, Vol. 71, No. 2016.06.003, pp. 1-19, 2016 "On the early diagnosis of Alzheimer's Disease from multimodal signals: A survey".

Annakutty A A. et al. International Journal of Pharma Medicine and Biological Sciences, Vol. 5, No. 3, pp. 178-183, 2016 "Review of Brain Imaging Techniques, Feature, Extraction and Classification Algorithms to Identify Alzheimer's Disease"

Gorelick P. et al. Biochemica et Biophysica Acta—Molecular Basis of Disease, Vol. 1862, No. 5, pp. 860-868, 2016 "Vascular cognitive impairment and dementia"

Adiukwu F. et al. World Journal of Psychiatry, Vol. 6, No. 2, pp. 199-207, 2016 "Vascular cognitive impairment, a cardiovascular complication"

Wimo A. et al. The Journal of the Alzheimer's Association, No. 2016.07.150, Online Publication, 2016 "The worldwide costs of dementia 2015 and comparisons with 2010".

WHO. et al. World Health Organization, Fact Sheets, 2015 "Mortality and global health estimates".

Horsburgh K. Alzheimer's Society, Research Project, 2015 "Vulnerability of the neurovascular unit to cerebral hypoperfusion: An early event in vascular dementia and Alzheimer's disease?".

Giet A. et al. Neurobiology of Aging, Vol. 36, No. 4, pp. 1619-1628, 2015 "Regional cerebral blood flow estimated by early PiB uptake is reduced in mild cognitive impairment and associated with age in an amyloid-dependent manner".

Winkler E A. Nature Neuroscience, Vol. 18, No. 4, pp. 521-530, 2015 "GLUT1 reductions exacerbate Alzheimer's disease vasculo-neuronal dysfunction and degeneration".

Holland P R. et al. Journal of the International Society of Cerebral Blood Flow and Metabolism, Vol. 35, No. 6, pp. 1005-1014, 2015 "Gliovascular disruption and cognitive deficits in a mouse model with features of small vessel disease".

Chen Shen T. Physical Review X, Vol. 4, No. 4-041033, 2014 "Anisotropic Complementary Acoustic Metamaterial for Canceling out Aberrating Layers"

den Abeelen A S. et al. Current Alzheimer Research, Vol. 11, No. 1, pp. 11-17, 2014 "Impaired Cerebral Autoregulation and Vasomotor Reactivity in Sporadic Alzheimer's Disease"

Hosseini S M H. Frontiers in Aging Neuroscience, Vol. 6, p. 231, 2014 "Neural Correlates of cognitive intervention in persons at risk of developing Alzheimer's disease"

Gallagher J. BBC News Website, Online Publication, No. health-29815518, 2014 "Dementia is leading cause of death for women"

Marmarelis V Z. Medical Engineering and Physics, Vol. 36, No. 5, pp. 628-637, 2014 "Model-based physiomarkers of cerebral hemodynamics in patients with mild cognitive impairment"

Gomez-Ramirez J. Frontiers in Aging Neuroscience, Vol. 6, No. 2014.00012, 2014 "Network-based biomarkers in Alzheimer's disease: review and future directions"

Bloom G S. Journal of the American Medical Association—JAMA Neurology, Vol. 71, No. 4, pp. 505-508, 2014 "Amyloid-μ and tau: the trigger and bullet in Alzheimer disease pathogenesis"

Obrig H. NeuroImage, Vol. 85, No. 1, pp. 535-546, 2014 "NIRS in clinical neurology—a 'promising' tool?"

Ehlis A C. NeuroImage, Vol. 85, No. 1, pp. 478-488, 2014 (Online 2013) "Application of functional near-infrared spectroscopy in psychiatry".

Pietrangelo S. Massachusetts Institute of Technology Libraries, Master of Science Thesis, 2013 "An electronically steered, wearable transcranial doppler ultrasound system".

Sheline Y I. et al. Biological Psychiatry, Vol. 74, No. 5, pp. 340-347, 2013 "Resting State Functional Connectivity in Preclinical Alzheimer's Disease"

Lin, A J. University of California, Irvine, ProQuest Dissertations Publishing, No. 3564576, 2013 "Spatial Frequency Domain Imaging: Applications in Preclinical Models of Alzheimer's Disease"

Sato N. et al. Frontiers in Aging Neuroscience, Online Publication, No. 5:64, 2013 "Vascular cognitive impairment, a cardiovascular complication"

Russell P. et al. BMJ Open, No. 3:e004023, 2013 "Improving the identification of people with dementia in primary care: evaluation of the impact of primary care dementia coding guidance on identified prevalence"

Kuruvilla M. Cognitive Neuroscience, Vol. 4, No. 2, pp. 115-121, 2013. "Neural correlates of cognitive decline in ALS: An fNIRS study of the prefrontal cortex"

Carmichael O. NeuroImage, Vol. 66, pp. 449-456, 2013. "Coevolution of brain structures in amnestic mild cognitive impairment"

Cordell C. et al. Journal of Alzheimer's Disease, Vol. 9, No. 2, pp. 141-150, 2013 "Alzheimer's Association recommendations for operationalizing the detection of cognitive impairment during the Medicare Annual Wellness Visit in a primary care setting"

Wang L. et al. JAMA Neurology, Vol. 70, No. 10, pp. 1242-1248, 2013 "Cerebrospinal Fluid Aβ42, Phosphorylated Tau181, and Resting-State Functional Connectivity"

Hallacoglu B. TUFTS University, ProQuest Dissertations Publishing, No. 3563615, 2013 "Noninvasive absolute cerebral oximetry with frequency-domain near-infrared spectroscopy"

Xiaowei S. et al. Journal of Alzheimer's Disease, Vol. 8, No. 4, Supplement, p. 35, 2012 "Cerebral blood flow changes in early Alzheimer's disease: a high-field arterial spin labeling perfusion MRI study"

Bateman R. The New England Journal of Medicine, Vol. 367, No. 8, p. 780, 2012 "Clinical and biomarker changes in dominantly inherited Alzheimer's disease"

van Beek A. Neurobiology of Aging, Vol. 33, No. 2, pp. 428.e21-428.e31, 2012 (Online 2011) "Oscillations in cerebral blood flow and cortical oxygenation in Alzheimer's disease"

Mazza M. et al. Journal of Alzheimer's Disease, Vol. 23, No. 3, pp. 375-389, 2011 "Primary Cerebral Blood Flow Deficiency and Alzheimer's Disease: Shadows and Lights"

Tripoloti E E. Artificial Intelligence in Medicine, Vol. 53, No. 1, pp. 35-45, 2011 et al. "A supervised method to assist the diagnosis and monitor progression of Alzheimer's disease using data from an fMRI experiment"

Dickstein D. Mount Sinai Journal of Medicine, Vol. 77, No. 1, pp. 82-102, 2010 "Role of Vascular Risk Factors and Vascular Dysfunction in Alzheimer's Disease"

Bell R D. et al. Acta Neuropathologica, Vol. 118, No. 1, pp. 103-130, 2009 "Neurovascular mechanisms and blood-brain barrier disorder in Alzheimer's disease"

Iadecola C. et al. Stroke—American Heart Association, Vol. 40(3 Suppl), S40-S44, 2009 "Threats to the Mind: Aging, Amyloid, and Hypertension"

Buckner R. et al. Annals of the New York Academy of Sciences, Vol. 1124, pp. 1-38, 2008 "The Brain's Default Network: Anatomy, Function, and Relevance to Disease"

Clifford P M. et al. Brain Research, Vol. 1142, No. 2007.01.070, pp. 223-236, 2007 "Abeta peptides can enter the brain through a defective blood brain barrier and bind selectively to neurons"

Allen G. et al. Archives of Neurology, Vol. 64, No. 10, pp 1482-1487, 2007 "Reduced hippocampal functional connectivity in Alzheimer disease"

Chow N. et al. Proceedings of the National Academy of Sciences of the United States of America, Vol. 104, No. 3, pp. 823-828, 2007 "Serum response factor and myocardin mediate arterial hypercontractility and cerebral blood flow dysregulation in Alzheimer's phenotype"

Wang K. et al. Human Brain Mapping, Vol. 28, No. 10, pp. 967-978, 2007 "Altered functional connectivity in early Alzheimer's disease: A resting-state fMRI study"

Arai H. et al. Brain and Cognition, Vol. 61, No. 2, pp. 189-194, 2006 "A quantitative near-infrared spectroscopy study: A decrease in cerebral hemoglobin oxygenation in Alzheimer's disease and mild cognitive impairment"

Hirao K. et al. NeuroImage, Vol. 28, No. 4, pp. 1014-1021, 2005 "The prediction of rapid conversion to Alzheimer's disease in mild cognitive impairment using regional cerebral blood flow SPECT"

Attems J. et al. Acta Neuropathologica, Vol. 110, No. 3, pp. 222-231, 2005 "Alzheimer's disease pathology influences severity and topographical distribution of cerebral amyloid angiopathy"

Zlokovic B V. Trends in Neurosciences, Vol. 28, No. 4, pp. 202-208, 2005 "Neurovascular mechanisms of Alzheimer's neurodegeneration"

Ruitenberg A. Annals of Neurology, Vol. 57, No. 6, pp. 789-794, 2005 "Cerebral Hypoperfusion and Clinical Onset of Dementia: The Rotterdam Study"

Johnson N A. Radiology, Vol 234, No. 3, pp 851-859, 2005 "Pattern of Cerebral Hypoperfusion in Alzheimer Disease and Mild Cognitive Impairment Measured with Arterial Spin-labeling MR Imaging: Initial Experience"

Zlokovic B V. Brain Pathology, Vol. 15, No. 1, pp. 78-83, 2005 "Neurovascular pathways and Alzheimer amyloid beta-peptide"

Parsons T. Aging, Neuropsychology, and Cognition, Vol. 12, No. 1, pp. 78-88, 2005 "Gender Differences and Cognition Among Older Adults"

Greenberg S M. Stroke, Vol. 35, No. 11, Supp. 1, pp. 2616-2619, 2004 "Amyloid Angiopathy-Related Vascular Cognitive Impairment"

Greicius M D. Proceedings of the National Academy of Sciences USA, Vol. 101, No. 13, pp. 4637-4642, 2004 "Default-mode network activity distinguishes Alzheimer's disease from healthy aging: evidence from functional MRI"

Herrmann M J. Brain Research Bulletin, Vol. 61, No. 1, pp. 51-56, 2003 "Frontal activation during a verbal-fluency task as measured by near-infrared spectroscopy"

Farkas E. et al. Progress in Neurobiology, Vol. 64, No. 6, pp. 575-611, 2001 "Cerebral microvascular pathology in aging and Alzheimer's disease"

De La Torre J C. Brain Research Reviews, Vol. 34, No. 3, pp. 119-136, 2000 "Evidence that Alzheimer's disease is a microvascular disorder: the role of constitutive nitric oxide"

Jaeger J J. et al. Neuroreport, Vol. 9, No. 12, pp. 2803-2807, 1998 "Sex differences in brain regions activated by grammatical and reading tasks"

Tamura M. et al. Philosophical Transactions of The Royal Society B: Biological Sciences Vol. 352, No. 1354, pp. 737-742, 1997 "Localized near-infrared spectroscopy and functional optical imaging of brain activity"

Vinters H V. et al. Ultrastructural Pathology, Vol. 18, No. 3, pp. 333-348, 1994 "Microvasculature in Brain Biopsy Specimens from Patients with Alzheimer's Disease: An Immunohistochemical and Ultrastructural Study"

Mathews P J. Brain and Language, Vol. 46, No. 3, pp. 439-462, 1994 "Wernicke and Alzheimer on the Language Disturbances of Dementia and Aphasia"

Hoshi Y. et al. Neuroscience Letters, Vol. 150, No. 1, pp. 5-8, 1993 "Detection of dynamic changes in cerebral oxygenation coupled to neuronal function during mental work in man"

Hachinski V C. Archives of Neurology, Vol. 32, No. 9, pp. 632-637, 1975 "Cerebral Blood Flow in Dementia"

What is claimed is:

1. An apparatus for collecting cerebral data from a patient for detecting neurocognitive disorders in the patient, the apparatus comprising a headset comprising:
   a plurality of sensors for collecting the cerebral data, the plurality of sensors including at least one ultrasonic sensor and at least one electromagnetic sensor;
   a processor for receiving the cerebral data collected from the plurality of sensors and transmitting the cerebral data to a remote processor,
   wherein the plurality of sensors are disposed upon the headset according to a pre-determined sensor distribution pattern that targets regions of the patient's brain including frontal, temporal, parietal, occipital, and cerebellar regions of the patient's brain.

2. The apparatus of claim 1, wherein the at least one ultrasonic sensor is a Transcranial Doppler and the headset further comprises at least one Doppler ultrasound transducer probe.

3. The apparatus of claim 1, wherein the at least one electromagnetic sensor is a Functional Near-Infrared Spectroscopic sensor.

4. The apparatus of claim 1, wherein the processor for receiving the collected cerebral data is further configured to generate and combine a timecode to the cerebral data collected from the plurality of sensors.

5. The apparatus of claim 1, wherein the processor includes a wireless transceiver operable to transmit the cerebral data to the remote processor.

6. The apparatus of claim 1, wherein the plurality of sensors is disposed on a plurality of arms connected to the headset, the plurality of arms arranged to surround the head of the patient.

7. The apparatus of claim 1, wherein the plurality of sensors is configured to operate simultaneously.

8. The apparatus of claim 1, wherein the plurality of sensors for collecting the cerebral data comprises at least one multimodal sensor configured to simultaneously detect, measure, collect and transmit at least two modalities of the cerebral data.

9. The apparatus of claim 1, wherein the processor further transmits a unique patient identifier to the remote processor.

10. A method for collecting cerebral data from a patient for detecting neurocognitive disorders in the patient, the method comprising:
   collecting the cerebral data via a plurality of sensors including at least one ultrasonic sensor and at least one electromagnetic sensor, the plurality of sensors disposed within a headset placed on the patient's head according to a pre-determined sensor distribution pattern that targets regions of the patient's brain including frontal, temporal, parietal, occipital and cerebellar regions of the patient's brain;
   associating the collected cerebral data with a generated timecode;
   comparing the cerebral data with historical cerebral data to determine a neurocognitive disorder detection score.

11. The method of claim 10, further comprising transferring the neurocognitive disorder detection score together with at least a unique identifier of the patient to a remote processor.

12. The method of claim 10, wherein historical cerebral data comprises a plurality of previously collected historical cerebral data and neurocognitive disorder detection scores.

13. The method of claim 10, wherein the at least one unique identifier of the patient includes a patient geolocation value and the remote processor includes a remote processor geolocation value.

14. The method of claim 1, wherein the patient geolocation value and the remote processor geolocation value are analyzed in concert, and the neurocognitive disorder detection score and the unique identifier is only transferred to the remote processor based on the patient geolocation value and the remote processor geolocation value.

15. The method of claim 10, wherein the cerebral data are integrated into the historical data.

16. A method for collecting cerebral data from a patient for detecting neurocognitive disorders in the patient, the method comprising:
   collecting the cerebral data via a plurality of sensors including at least one ultrasonic sensor and at least one electromagnetic sensor, the plurality of sensors disposed within a headset placed on the patient's head in accordance with a pre-determined sensor distribution pattern that targets regions of the patient's brain including frontal, temporal, parietal, occipital and cerebellar regions of the patient's brain;

associating the collected cerebral data with a generated timecode;

processing the cerebral data according to a machine learning classification process;

comparing the cerebral data with historical cerebral data to determine a neurocognitive disorder detection score.

17. The method of claim 16, wherein the machine learning classification process applies signal processing means for filtering the cerebral data as a pre-processing step.

18. The method of claim 16, wherein the machine learning classification process analyzes the cerebral data according to a programmed instruction set in order to extract and quantify cerebral data features from the cerebral data as a feature extraction step.

19. The method of claim 16, wherein the machine learning classification process processes the cerebral data according to unsupervised learning algorithms in order to detect key features.

20. The method of claim 19, wherein the unsupervised learning algorithms includes Unsupervised Bayesian learning, clustering, graph-theory method, or any combination thereof.

21. The method of claim 16, wherein the machine learning classification process processes the cerebral data according to supervised learning algorithms in order to detect key features.

22. The method of claim 21, wherein the supervised learning algorithms include Bayesian Classifiers, non-parametric approaches, K-nearest Neighbor, linear discriminant analyses, neural networks, deep neural networks, non-metric methods, or any combination thereof.

23. The method of claim 16, wherein at least one of the neurocognitive disorder detection score and the cerebral data are integrated into the historical data.

24. A system for detecting neurocognitive disorders in a patient, the system comprising:

a headset comprising:
  a plurality of sensors for collecting cerebral data, the plurality of sensors including at least one ultrasonic sensor and at least one electromagnetic sensor disposed upon the headset according to a pre-determined sensor distribution pattern that targets regions of the patient's brain including frontal, temporal, parietal, occipital and cerebellar regions of the patient's brain;
  a processing unit for receiving the collected cerebral data and transmitting the cerebral data collected from the plurality of sensors to a computer, the computer configured for receiving the cerebral data from the transceiver, the computer comprising:
  a processor configured to detect and analyze key features of the cerebral data to determine a neurocognitive disorder probability score and a neurocognitive disorder progress score based on the key features of the cerebral data and historical cerebral data.

* * * * *